(12) United States Patent
Sasaki et al.

(10) Patent No.: US 12,333,131 B2
(45) Date of Patent: Jun. 17, 2025

(54) AUTOMATED ANALYZER DISPLAYING A GUI INCLUDING FIRST AND SECOND INSPECTION INFORMATION

(71) Applicant: HITACHI HIGH-TECH CORPORATION, Tokyo (JP)

(72) Inventors: Shunsuke Sasaki, Tokyo (JP); Taku Sakazume, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 118 days.

(21) Appl. No.: 17/626,146

(22) PCT Filed: Feb. 21, 2020

(86) PCT No.: PCT/JP2020/007029
§ 371 (c)(1),
(2) Date: Jan. 11, 2022

(87) PCT Pub. No.: WO2021/029093
PCT Pub. Date: Feb. 18, 2021

(65) Prior Publication Data
US 2022/0244840 A1  Aug. 4, 2022

(30) Foreign Application Priority Data
Aug. 9, 2019   (JP) .................................. 2019-147021

(51) Int. Cl.
*G01N 35/10* (2006.01)
*G01N 35/00* (2006.01)
(Continued)

(52) U.S. Cl.
CPC ... *G06F 3/04847* (2013.01); *G01N 35/00722* (2013.01); *G01N 35/1002* (2013.01);
(Continued)

(58) Field of Classification Search
None
See application file for complete search history.

(56) References Cited

U.S. PATENT DOCUMENTS 6,080,364 A * 6/2000 Mimura ............... G01N 35/026
422/65
6,442,440 B1   8/2002 Miller
(Continued)

FOREIGN PATENT DOCUMENTS

CN    102483423 A    5/2012
JP    2004-0502179 A    1/2004
(Continued)

OTHER PUBLICATIONS

International Search Report of PCT/JP2020/007029 dated May 12, 2020.
(Continued)

*Primary Examiner* — Henry Orr
(74) *Attorney, Agent, or Firm* — MATTINGLY & MALUR, PC (57) ABSTRACT

The automated analyzer comprises: an analysis operation unit for analyzing a reaction liquid, control unit for controlling the operation of the analysis operation unit, a storage unit for storing analysis results from the analysis operation unit and information about a consumable used by the analysis operation unit, and a display unit for displaying the analysis results and inspection information. The control unit generates an inspection information display GUI including a first inspection information display area for displaying first inspection information from among the inspection information and a second inspection information display area for displaying second inspection information, which is different from the first inspection information, from among the inspection information, controls the display unit such that when the inspection information display GUI is displayed on
(Continued)

the screen of the display unit, the first inspection information and second inspection information are displayed in different display formats.

5 Claims, 10 Drawing Sheets (51) Int. Cl.
*G06F 3/04847* (2022.01)
*G06F 3/0485* (2022.01)
(52) U.S. Cl.
CPC ... *G06F 3/0485* (2013.01); *G01N 2035/0091* (2013.01); *G06F 2203/04803* (2013.01)

(56) References Cited

U.S. PATENT DOCUMENTS

| | | | | |
|---|---|---|---|---|
| 6,579,717 | B1* | 6/2003 | Matsubara | G01N 35/026 |
| | | | | 198/349.5 |
| 8,706,303 | B2 | 4/2014 | Kuwano et al. | |
| 10,866,719 | B1* | 12/2020 | Bulusu | H04L 51/52 |
| 10,962,559 | B2* | 3/2021 | Nehashi | G01N 35/0092 |
| 2005/0039135 | A1* | 2/2005 | Othmer | H04M 1/72469 |
| | | | | 715/831 |
| 2007/0264956 | A1* | 11/2007 | Bicker | G06Q 10/10 |
| | | | | 455/186.1 |
| 2008/0071503 | A1 | 3/2008 | Fujita et al. | |
| 2010/0271479 | A1 | 10/2010 | Heydlauf | |
| 2010/0281421 | A1* | 11/2010 | Lin-Hendel | G06F 3/0482 |
| | | | | 715/785 |
| 2011/0169836 | A1 | 7/2011 | Orihashi et al. | |
| 2011/0275920 | A1* | 11/2011 | Jennewine | G16H 20/17 |
| | | | | 600/365 |
| 2012/0010899 | A1 | 1/2012 | Minato et al. | |
| 2012/0324507 | A1* | 12/2012 | Weber | H04N 21/4312 |
| | | | | 725/37 |
| 2013/0009988 | A1 | 1/2013 | Tokunaga et al. | |
| 2014/0100791 | A1 | 4/2014 | Darmstadt et al. | |
| 2014/0147335 | A1* | 5/2014 | Sarwar | G01N 35/00584 |
| | | | | 422/63 |
| 2014/0152820 | A1 | 6/2014 | Heydlauf | |
| 2014/0258890 | A1* | 9/2014 | Kamdar | G06F 3/0485 |
| | | | | 715/760 |
| 2015/0377771 | A1 | 12/2015 | Orihashi et al. | |
| 2016/0300027 | A1 | 10/2016 | Jensen et al. | |
| 2017/0351395 | A1* | 12/2017 | Giannopoulos | G06F 3/04845 |
| 2020/0026397 | A1* | 1/2020 | Wohlstadter | G16C 20/10 |

FOREIGN PATENT DOCUMENTS

| | | |
|---|---|---|
| JP | 2008-051723 A | 3/2008 |
| JP | 2010-156649 A | 7/2010 |
| JP | 2011-508881 A | 3/2011 |
| JP | 2012-021815 A | 2/2012 |
| JP | 2015-099160 A | 5/2015 |
| JP | 2018-163157 A | 10/2018 |

OTHER PUBLICATIONS

Extended European Search Report received in corresponding European Application No. 20851378.8 dated Jul. 26, 2023.
Chinese Office Action received in corresponding Chinese Application No. 202080055356.9 dated Dec. 18, 2024.

* cited by examiner

AUTOMATED ANALYZER DISPLAYING A GUI INCLUDING FIRST AND SECOND INSPECTION INFORMATION

TECHNICAL FIELD

The present disclosure relates to an automated analyzer.

BACKGROUND ART

An automated analyzer not only displays analysis results on a GUI screen of a display unit, but also displays all kinds of information such as a consumable and alarm information used for the analysis. A user (operator) is accessing information to be known by operating a plurality of buttons displayed on the GUI screen to transition the screen.

For example, PTL 1 discloses an automated analyzer that displays a GUI having a general function button, a specific function button, and a scrollable text area for displaying an information message on a screen. As described above, according to PTL 1, by always displaying the function button for displaying information on a function of the automated analyzer on the screen, the user can access the screen that displays the information with a minimum operation of the user.

CITATION LIST

Patent Literature

PTL 1: JP-T-2004-502179

SUMMARY OF INVENTION

Technical Problem

However, when a technique of PTL 1 is used, it is not possible to immediately determine whether an event that the user needs to immediately respond to occurs from a normally displayed screen, and this may lead to device stopping and result communication delay. In addition, with the increasing number of functions of automated analyzers in recent years, it is possible to display a large amount of information, there is a problem that complicated screen operations is required until the user accesses information that the user wants to know and it takes time.

The disclosure provides an automated analyzer with which risks of device stopping and result communication delay are reduced in view of these circumstances.

Solution to Problem

TO solve the above problem, the disclosure provides an automated analyzer including: an analysis operation unit configured to analyze a reaction liquid obtained by dispensing a reagent and a sample into a reaction vessel; a control unit configured to control an operation of the analysis operation unit; a storage unit configured to store analysis results from the analysis operation unit and information on a consumable used by the analysis operation unit; and a display unit configured to display the analysis results and inspection information, wherein the control unit is configured to, generate an inspection information display GUI including a first inspection information display area for displaying first inspection information from among the inspection information and a second inspection information display area for displaying second inspection information, which is different from the first inspection information, from among the inspection information, and control the display unit such that when the inspection information display GUI is displayed on a screen of the display unit, the first inspection information and the second inspection information are displayed in different display formats.

Advantageous Effect

According to a technique of the disclosure, the automated analyzer can reduce risks of device stopping and result communication delay.

DESCRIPTION OF EMBODIMENTS

Hereinafter, embodiments of the disclosure will be described with reference to drawings. Hereinafter, an automated immunological analyzer will be described as an example, but the disclosure is not limited to this, and the disclosure includes a wide range of devices that react a sample with a reagent and analyze the sample based on a result of the reaction. For example, the disclosure also includes a biochemical automated analyzer, a mass spectrometer used for a clinical laboratory test, a coagulation analyzer for measuring blood coagulation time, and the like. In addition, the disclosure can also be applied to a combined system that combines the mass spectrometer and the coagulation analyzer with the biochemical automated analyzer and the automated immunological analyzer, or an automated analysis system to which these devices are applied.

(1) First Embodiment

<Configuration Example of Automated Analyzer>

Figure 1:
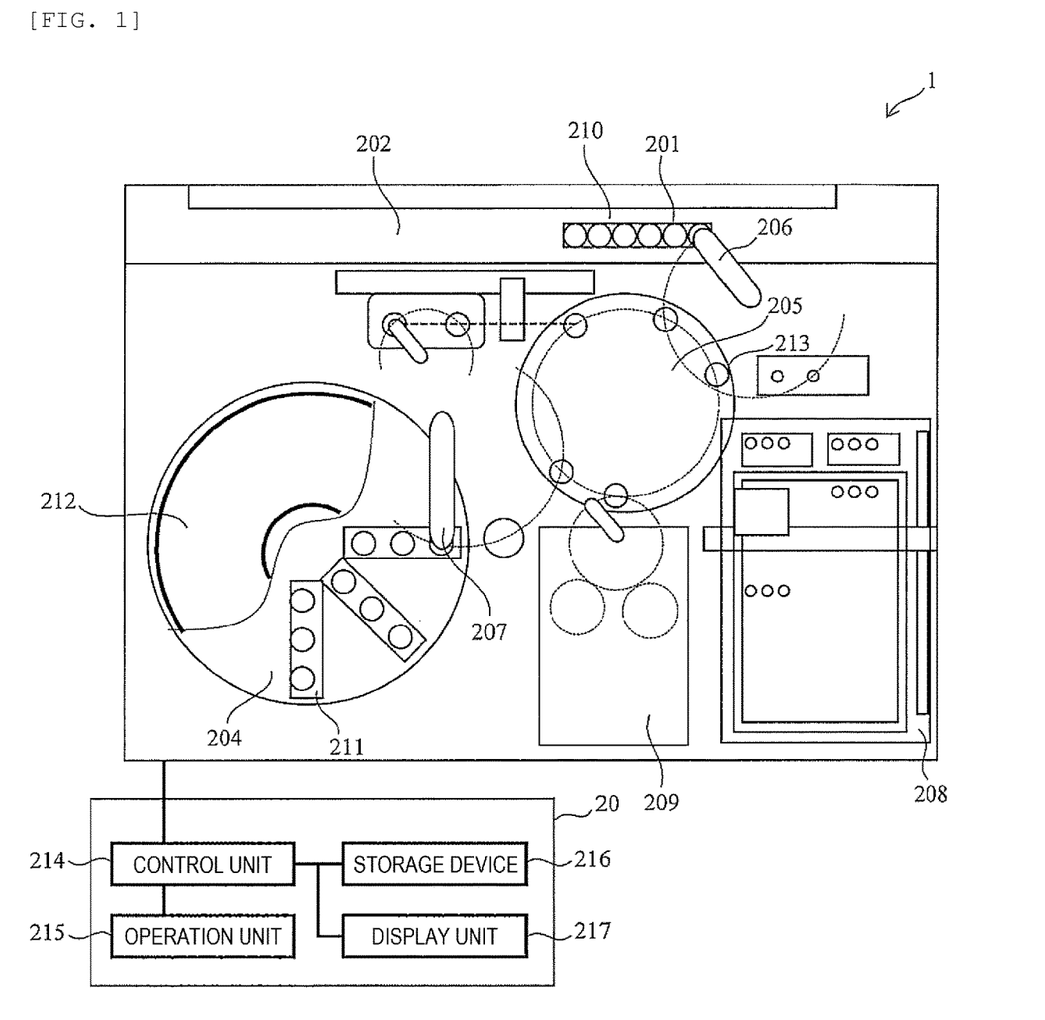
FIG. 1 is a diagram showing a schematic configuration example of an automated analyzer 1.

FIG. 1 is a diagram showing a schematic configuration example of an automated analyzer 1. As shown in FIG. 1, the automated analyzer 1 includes a rack transport line 202 for transporting a rack 201, a reagent storage unit (reagent cold insulation unit) 204, an incubator (reaction disk) 205, a sample dispensing unit (sample dispensing unit) 206, a reagent dispensing unit 207, a transport unit 208 for transporting a consumable, and an analysis unit 209, and these units are referred to as analysis operation units.

The rack 201 accommodates a plurality of sample vessels 210 that accommodate biological samples (samples) such as blood and urine, and is transported on the rack transport line 202 in a state in which the sample vessels 210 are accommodated.

The reagent storage unit 204 is a reagent vessel storage unit, and accommodates and colds the plurality of reagent vessels 211 in which various reagents used for sample analysis are accommodated. At least a part of an upper surface of the reagent storage unit 204 is covered with a reagent disc cover 212.

The incubator 205 has a reaction vessel arrangement unit in which a plurality of reaction vessels 213 for reacting a sample and a reagent are arranged (not shown: a plurality of holes provided on a disc to arrange the reaction vessels), and a temperature adjusting mechanism for adjusting a temperature of the reaction vessels 213 to a desired temperature.

The sample dispensing unit 206 can dispense the sample from the sample vessels 210 to the reaction vessels 213 accommodated in the incubator 205 by a rotation drive mechanism or a vertical drive mechanism. In addition, similarly, the reagent dispensing unit 207 can dispense the reagent from the reagent vessels 211 to the reaction vessels 213 accommodated in the incubator 205 by the rotation drive mechanism or the vertical drive mechanism. The analysis unit 209 includes a photomultiplier tube, a light source lamp, a spectrometer, and a photodiode, has a function of adjusting their temperatures, and analyzes a reaction liquid.

In addition to the analysis operation unit described above, the automated analyzer 1 includes a computer (hereinafter, referred to as a PC) 20 that controls an operation of the entire automated analyzer 1. The PC 20 includes a control unit 214, an operation unit 215, a storage device 216, and a display unit (display device) 217.

The storage device 216 includes a hard disk, a memory, and the like. In addition, the storage device 216 may store, for example, a temperature range corresponding to each unit.

The operation unit 215 includes input devices such as a mouse and a keyboard, and is configured such that a user (operator) can input desired data, information, and an instruction. For example, when the display unit 217 is configured by a liquid crystal display or the like, the display unit 217 can be a touch panel, and in this case, the display unit 217 constitutes a part of the operation unit 215.

The control unit 214 may be configured as hardware by a dedicated circuit board, or may be configured by the software executed by the PC connected to the automated analyzer 1. When the control unit 214 is configured by the hardware, the control unit 214 can be realized by integrating a plurality of arithmetic units that execute a processing on a wiring board, in a semiconductor chip or a package. When the control unit 214 is configured by the software, the control unit 214 can be realized by mounting a processor such as a high-speed general-purpose CPU on the PC and executing a program that executes a desired arithmetic processing. It is also possible to upgrade an existing device with a recording medium on which this program is recorded. In addition, these devices, circuits, and PCs are connected by a wired or wireless network, and transmit and receive data appropriately. In addition, the PC 20 can be connected to a high-level system such as a clinical laboratory test information system, and can transmit and receive test information including instrument status, consumable information, and measurement information.

<Configuration Example of GUI>

Figure 2:
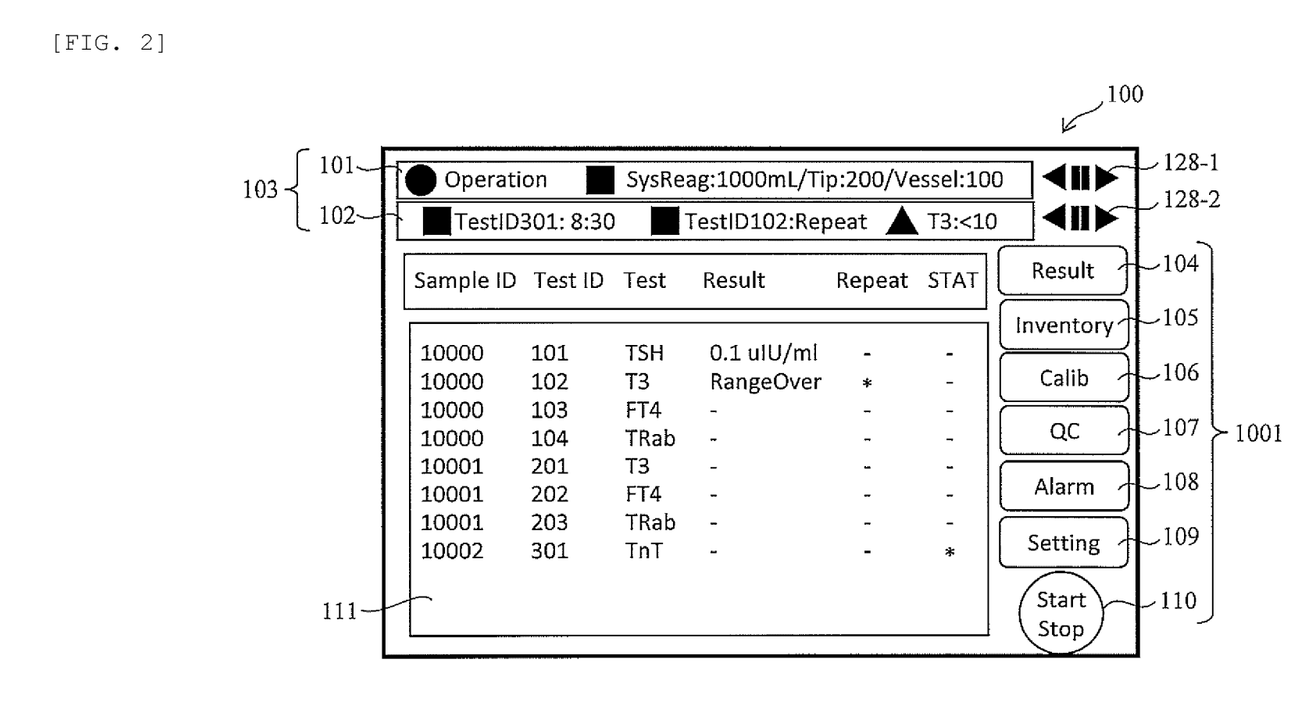
FIG. 2 is a diagram showing a configuration example of an inspection information display GUI 100 displayed on a display screen of a display unit 217 of the automated analyzer 1 to which an inspection information display method according to the present embodiment is applied.

FIG. 2 is a diagram showing a configuration example of the inspection information display graphical user interface (GUI) 100 displayed on a display screen of the display unit 217 of the automated analyzer 1 to which an inspection information display method according to the present embodiment is applied. The inspection information display GUI 100 includes, as configuration items, (i) an inspection information display area 103 including a first inspection information display unit 101 and a second inspection information display unit 102, (ii) a global icon display area 1001 that includes icons for transitioning to various detailed information screens of a measurement result 104, consumable information 105, calibration information 106, quality control information 107, and alarm information 108 on a right side of the display unit, a setting button 109, and measurement start/stop 110, and displays the icons for setting various devices, and (iii) a detailed information display area 111 at the center of a screen of the inspection information display GUI.

When the icons displayed in the global icon display area 1001 is selected by the user, the display unit 217 displays detailed information corresponding to the selected icons in the detailed information display area 111. FIG. 2 shows an example in which the measurement result 104 is selected and the measurement result is displayed in the detailed information display area 111. The global icon display area 1001 is an area for displaying a fixed item regardless of display contents of the inspection information display area 103 and the detailed information display area 111.

The inspection information display area 103 is an area for displaying a content described below regardless of the display content of the detailed information display area 111. The inspection information display area 103 includes the first inspection information display unit 101 and the second inspection information display unit 102, and is configured to display the inspection information having different contents in different display formats.

The transition to the screen of the detailed information is realized by the user selecting one of the display contents displayed on the first inspection information display unit 101 and the second inspection information display unit 102. For example, when the display of the alarm information is selected, the screen transitions to a detailed display screen of a detailed content of an alarm and a coping method thereof, and when the display of the measurement information is selected, the screen transitions to the detailed display screen of the measurement result. In addition, regarding the display in which the user determines that it is not necessary to confirm the detailed information, the display contents displayed in the first inspection information display unit 101 and the second inspection information display unit 102 can be deleted by the user selecting the display contents. At that time, it is possible to distinguish selection methods of the transition and deletion of the detailed information screen from each other. For example, when the user clicks once, the screen transitions to the detailed information screen, and when the user double-clicks, the corresponding detailed information display can be deleted.

Further, the inspection information display GUI 100 includes stop/play buttons 128-1 and 128-2. When the user operates the stop/play buttons 128-1 and 128-2, the display displayed on the first inspection information display unit 101 and the second inspection information display unit 102 can be stopped, played, and rewound. For example, the stop/play button 128-1 is provided for the first inspection information display unit 101, and the stop/play button 128-2 is provided for the second inspection information display unit 102, and the stop/play button 128-1 and the stop/play button 128-2 can individually perform the stop and play operations of the display. In addition, when the display unit 217 has a touch panel function (when the display unit 217 constitutes a part of the operation unit 215), the display unit 217 may be configured to have the same function as the stop/play buttons 218-1 and 218-2 by swiping the screen of the display unit 217. When the user misses the displayed information or wants to stop and confirm the information, the stop/play button 128 can surely confirm the information.

In addition, the user can set the inspection information to be displayed. The information to be known (the type of information to be checked frequently or the type of information to be considered important) differs depending on the user who uses the automated analyzer 1. Therefore, displaying (displaying uniformly) uniform information (fixed information) leads to displaying unnecessary information depending on the user, and there is a possibility that important information may be missed. That is, since the inspection information to be displayed can be set by the user, it is easier to more efficiently prioritize the displayed information.

<Example of Setting Screen>

FIGS. 3 to 8 are diagrams showing configuration examples of display inspection information setting screens 120 to 170 for setting inspection information to be displayed. The display inspection information setting screens 120 to 170 can be displayed by selecting the setting button 109 displayed in the global icon display area 1001 and passing through various setting screens (not shown).

The inspection information can be classified into, for example, the instrument status, the consumable information, the measurement information, the alarm information, and the like. Therefore, classifications (categories) of various inspection information is displayed in an inspection information display area 1002 at an upper portion of the setting screen, and when each classification is selected, more detailed display information can be selected. For example, the inspection information display area 1002 includes classification setting buttons (for example, instrument status 112, consumable information 113, measurement information 114, and alarm information 115) that can transition to the setting screens 120 to 170 for each classification. When the user selects any of the instrument status 112, the consumable information 113, the measurement information 114, or the alarm information 115, the control unit 214 displays the setting screen corresponding to the classification setting button. For example, in the classification of the instrument status 112, it is possible to set whether to display a status related to an instrument, for example, the instrument status such as during measurement, standby, and waiting for measurement. In addition, in the classification of consumable information (Inventory) 113, it is possible to display and set information on a calibration, an assay reagent, a solid consumable, and a waste. The measurement information (Test Info) 114 and the alarm information (Alarm) 115 will be described later.

(i) Calibration Setting of Consumable Information (Inventory) 113

Figure 3:
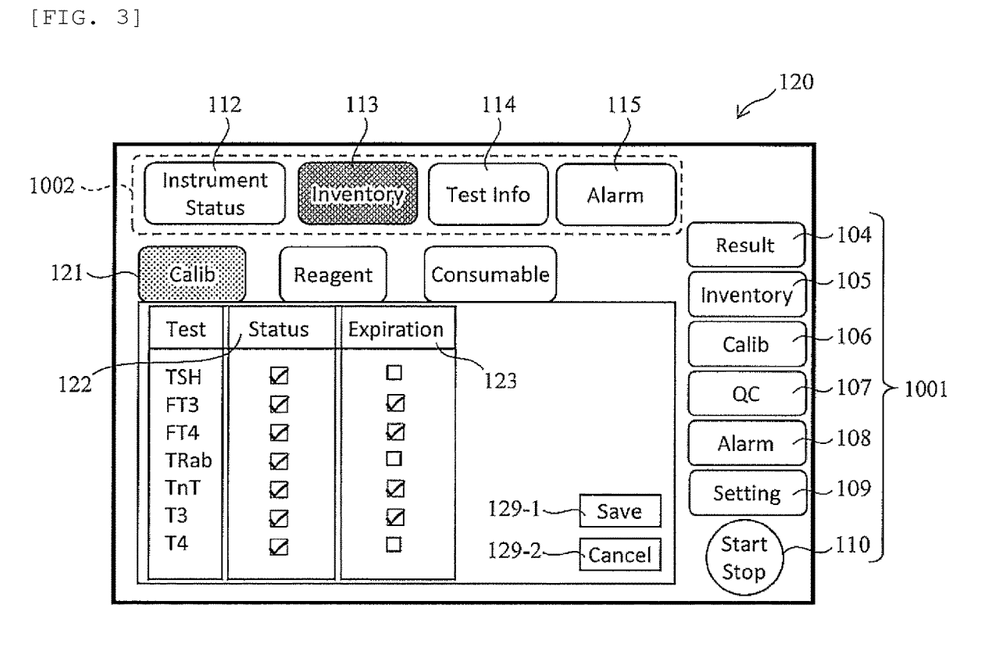
FIG. 3 is a diagram showing a configuration example of a calibration information setting screen 120 for setting calibration information of a consumable 113.

FIG. 3 is a diagram showing a configuration example of a calibration information setting screen 120 for setting calibration information on the consumable (using the assay reagent as an example) 113.

In a calibration information setting 121, for example, it is possible to display and set a calibration status (Status) 122 and an expiration date (Expiration) 123 can be set. In the calibration status (Status) 122, validity/invalidity of the calibration is displayed for each corresponding assay. In addition, in the expiration date (Expiration) 123, the expiration date or the number of days until the expiration date is displayed.

(ii) Assay Reagent Setting for Consumable Information (Inventory) 113

Figure 4:
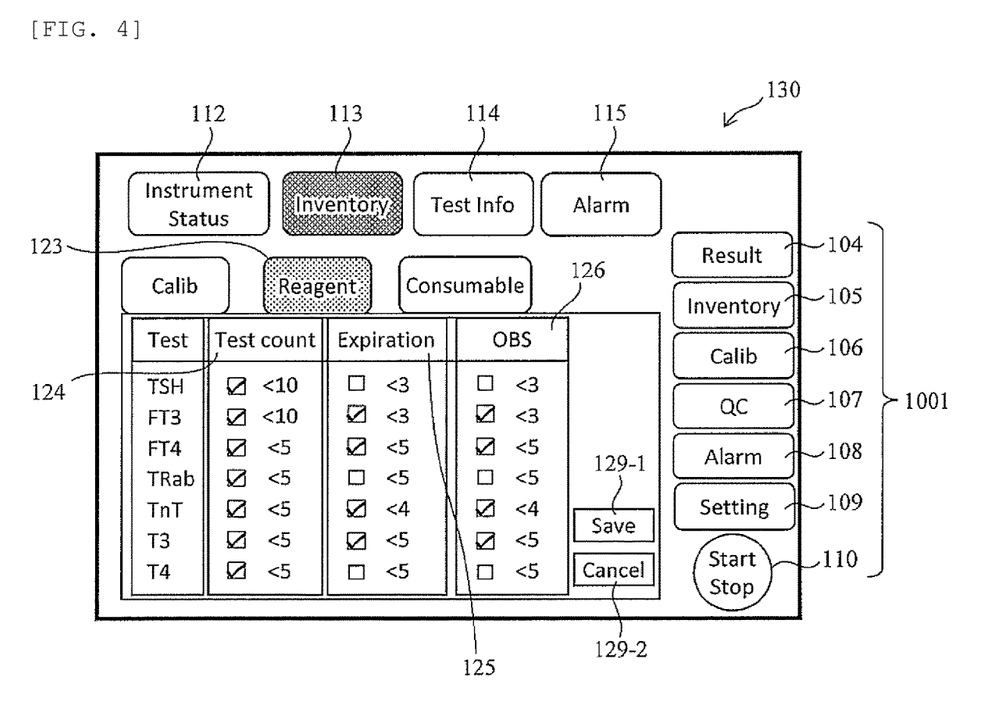
FIG. 4 is a diagram showing a configuration example of an assay reagent information setting screen 130 for setting assay reagent information of the consumable 113.

FIG. 4 is a diagram showing a configuration example of an assay reagent information setting screen 130 for setting information on the assay reagent of the consumable 113.

In the classification of the assay reagent (Reagent) 123, it is possible to set whether to display information on, for example, a remaining amount (Test Count) 124 of the assay reagent, an expiration date (Expiration) 125, and an on-board expiration date (OBS; expiration date from reagent opening date) 126.

In the remaining amount (Test Count) 124 of the assay reagent, a threshold value for displaying a remaining amount on the first inspection information display unit 101 or the second inspection information display unit 102 can also be set. When the remaining amount of the assay reagent is below the threshold value, a display indicating that the remaining amount is small, for example, Level Low or a specific remaining amount is displayed on the first inspection information display unit 101 or the second inspection information display unit 102.

In the expiration date (Expiration) 125, a threshold value for displaying the number of days until the expiration date on the first inspection information display unit 101 or the second inspection information display unit 102 can also be set. When the expiration date of the assay reagent is below the threshold value, a display indicating that the expiration date is approaching, such as Expire or a specific number of days, is displayed on the first inspection information display unit 101 or the second inspection information display unit 102.

In the on-board expiration date 126, a threshold value for displaying the number of days until the on-board expiration date on the first inspection information display unit 101 or the second inspection information display unit 102 can also be set. When the on-board expiration date of the assay reagent is below the threshold value, a display indicating that the expiration date is approaching, for example, OBS or a specific number of days, is displayed on the first inspection information display unit 101 or the second inspection information display unit 102.

(iii) Consumable Information Setting of Consumable Information (Inventory) 113

Figure 5:
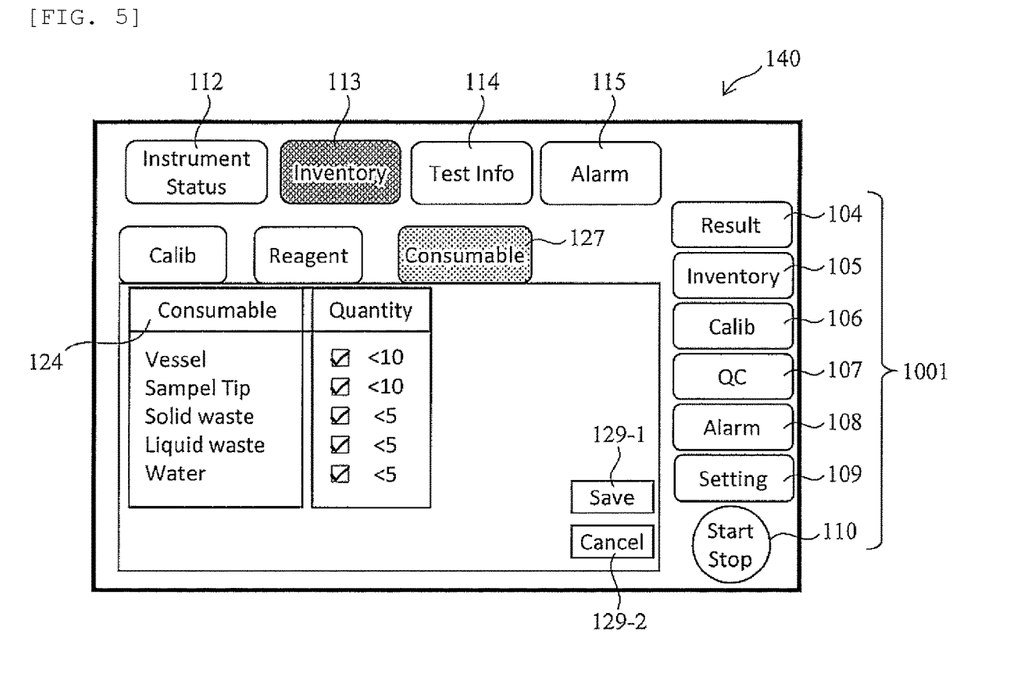
FIG. 5 is a diagram showing a configuration example of a consumable information setting screen 140 for setting solid consumable information 127 in consumable information.

FIG. 5 is a diagram showing a configuration example of a consumable information setting screen 140 for setting solid consumable information (Consumable) 127 in the consumable information (Inventory).

In the classification of the solid consumable information (Consumable) 127, it is possible to set whether to display information on consumables, such as a remaining amount of the reaction vessel (Vessel) used for measurement, a remaining amount of a dispensing tip (Sample Tip) for sample dispensing, a remaining number of waste vessels (Solid Waste) in which the reaction vessel and the dispensing tip are discarded, and a waste capacity (Liquid Waste) of the waste liquid tank in which waste liquid generated in measurement is collected.

For each item, the threshold value for displaying the remaining amount on the first inspection information display unit 101 or the second inspection information display unit 102 can also be set. When the remaining amount of each consumable is below the threshold value, a display indicating that the remaining amount is small, for example, abbreviations such as Vessel Short and Tip Short, a specific remaining amount, and the like are displayed on the first inspection information display unit 101 or the second inspection information display unit 102.

(iv) Setting Screen of Measurement Information (Test Info) 114

Figure 6:
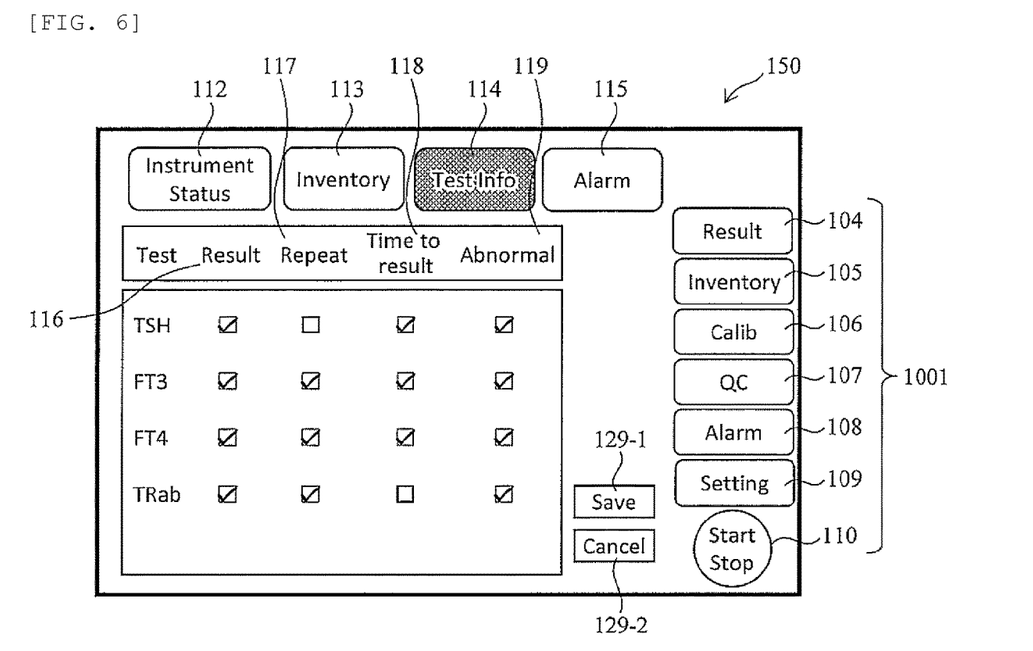
FIG. 6 is a diagram showing a configuration example of a measurement information setting screen 150 for setting measurement information 114.

FIG. 6 is a diagram showing a configuration example of a measurement information setting screen 150 for setting the measurement information (Test Info) 114.

In the classification of the measurement information (Test Info) 114, for all the measurement items registered in the automated analyzer 1, it is possible to select whether to display a measurement result (Result) 116, a re-inspection (Repeat: display related to whether to re-inspect when the measurement result is considered to be unsatisfactory) 117, a result output time (Time to Result: display made in view of the face that time until the result is output for each reagent is different, and the required time based on execution of another test is accumulated in the device) 118, and a sample error (Abnormal: display for recognizing which combination of which sample and which reagent causes an error) 119.

In the measurement result 116, a qualitative determination result (positive/negative/gray zone) and a quantitative result (concentration) are displayed. In the re-inspection 117, an occurrence of re-inspection and re-inspection conditions (dilution rate, or the like) are displayed. In the result output time 118, the time until the result is output is displayed. In the sample error 119, an occurrence of a sample-derived error such as insufficient sample amount or abnormal suction of samples is displayed.

(v) Setting Screen of Alarm Information (Alarm)

Figure 7:
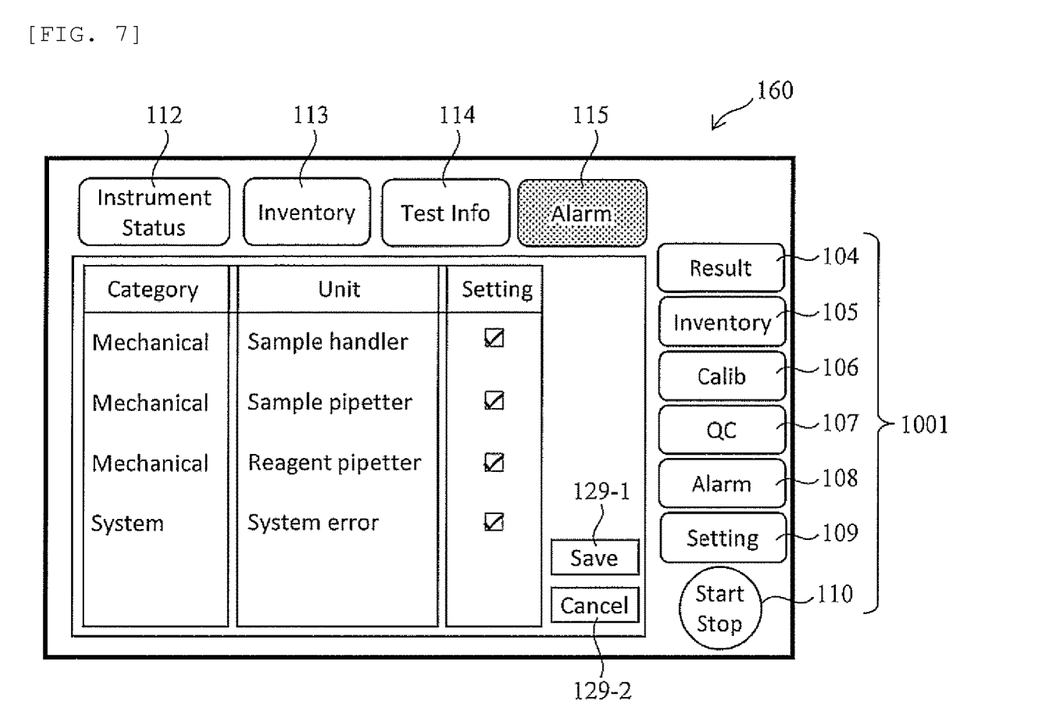
FIG. 7 is a diagram showing a configuration example of an alarm information setting screen 160 for setting alarm information 115.

FIG. 7 is a diagram showing a configuration example of an alarm information setting screen 160 for setting the alarm information (Alarm) 115.

In the classification of the alarm (Alarm) 115, it is possible to select whether to display all alarms defined in the automated analyzer 1. The setting may be set individually for each alarm, or may be displayed and set for each alarm category. The error in the category "device (System)" corresponds to an unexpected error that cannot be classified into a machine error or a software error. In addition, a device error for which it is not known what kind of error can be classified into the "device (System)".

(vi) Display Speed Setting Screen

Figure 8:
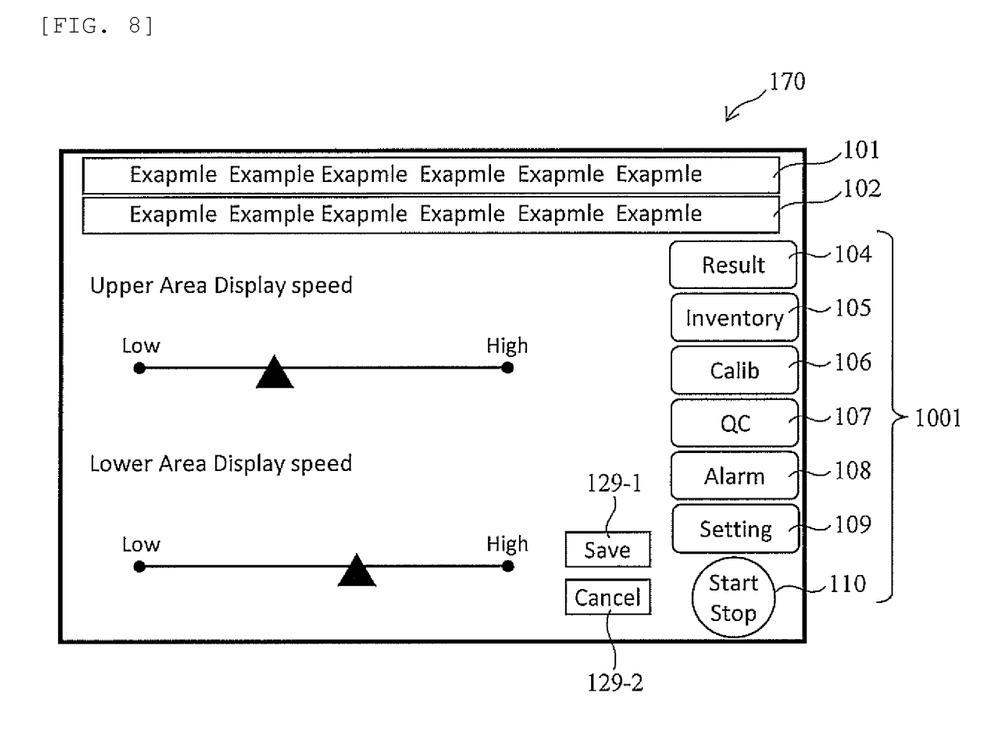
FIG. 8 is a diagram showing a configuration example of a display speed setting screen 170 for setting a display speed in a first inspection information display unit 101 or a second inspection information display unit 102.

FIG. 8 is a diagram showing a configuration example of a display speed setting screen 170 for setting a display speed in the first inspection information display unit 101 or the second inspection information display unit 102.

In order to display a large amount of inspection information in a limited display area, the first inspection information display unit 101 and the second inspection information display unit 102 can display various types of inspection information while moving them from the right to the left of each inspection information display unit. It should be noted that it may be moved from the left to the right.

In addition, in order to improve visibility of the user, display moving speeds of the first inspection information display unit 101 and the second inspection information display unit 102 can be set to different speeds and optional speeds by using the display speed setting screen 170. For example, the information displayed on the first inspection information display unit 101 can be set to be displayed in a moving manner at a first speed (high speed), and the information displayed on the second inspection information display unit 102 can be set to be displayed in a moving manner at a second speed (normal speed). In addition, when the display speed is set using the display speed setting screen 170, by displaying a predetermined example sentence at a speed set in the first inspection information display unit 101 and the second inspection information display unit 102 (FIG. 8), the user can confirm whether the display is set to be performed at a speed according to his/her preference.

Further, for the user, a configuration may be provided such that matters and items that need to be handled by the user, for example, information on shortage of consumable and sample error, and the information among the information displayed on the first inspection information display unit 101 and the second inspection information display unit 102 can be highlighted (for example, displayed in a color different from that of the other inspection information, displayed in a blinking manner, displayed in a rotating manner, and the like). As a result, it is possible to prompt the user to take an immediate response.

In addition, the user can set on which of the first inspection information display unit 101 or the second inspection information display unit 102 the display contents set by using the display speed setting screen 170 is to be display. For example, by setting information on important matters that need to be handled by the user to be displayed on the second inspection information display unit 102, a priority of the displayed information can be more easily recognized. At this time, the display speed of the second inspection information display unit 102 can be set larger than the display speed of the first inspection information display unit 101.

<Details of Display Processing>

Figure 9:
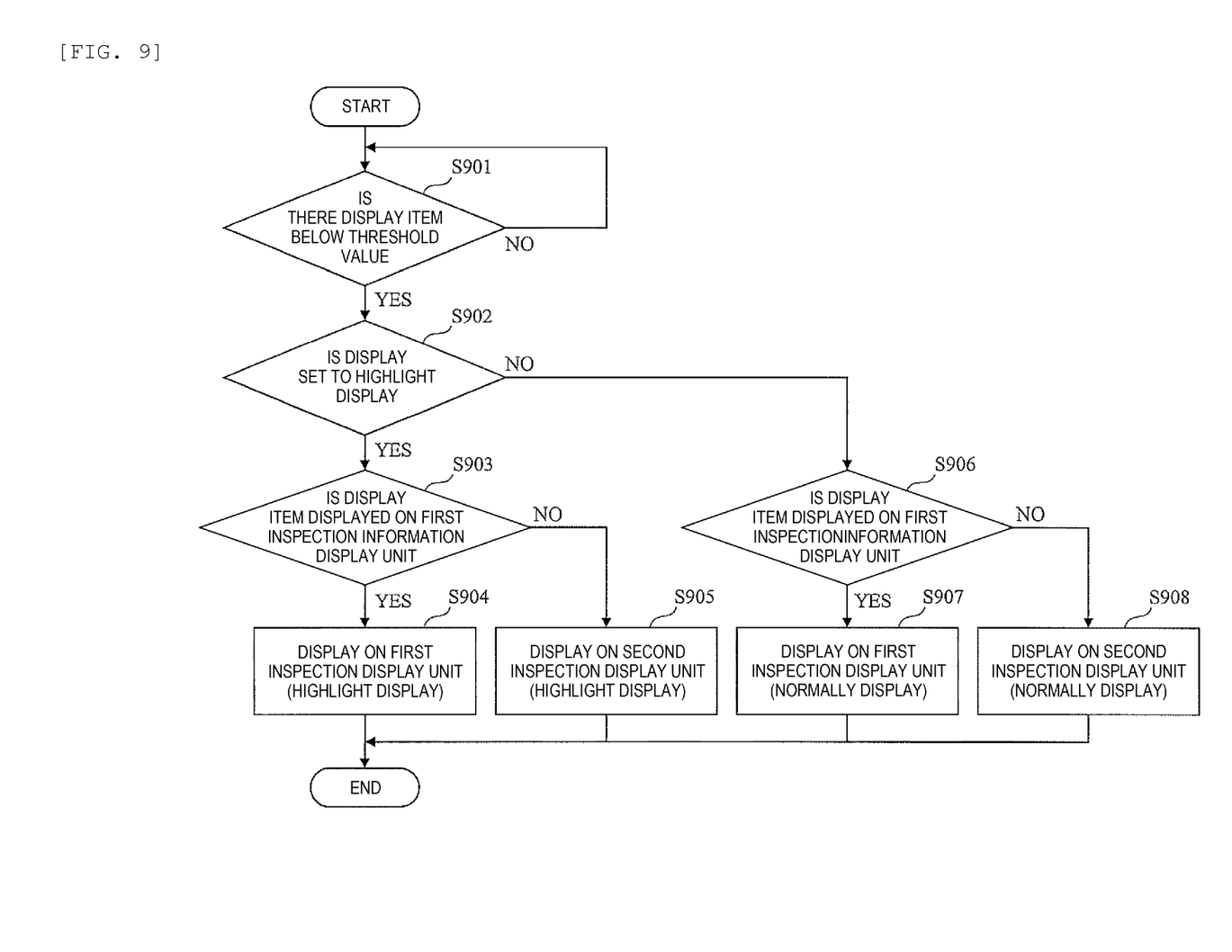
FIG. 9 is a flowchart illustrating an example of a display processing of inspection information in the inspection information display GUI 100.

FIG. 9 is a flowchart illustrating an example of a display processing of the inspection information in the inspection information display GUI 100. In the following flowcharts, it will be described that an operation subject of each step is the control unit 214.

(i) Step 901

The control unit 214 determines whether there is an item below the threshold value among the inspection information to be displayed. This determination processing can be set to be performed periodically, for example. If there is a display item below the threshold value (YES in step 901), the process proceeds to step 902. If there is no display item below the threshold value (NO in step 901), the control unit 214 periodically executes the determination processing.

(ii) Step 902

The control unit 214 confirms the content set by the user according to the display speed setting screen 170, and determines whether the highlight display is set for a target display item. If the highlight display is set (YES in step 902), the process proceeds to step 903. If the highlight display is not set (NO in step 902), the process proceeds to step 906.

(iii) Step 903

The control unit 214 confirms the content set by the user according to the display speed setting screen 170, and determines whether a display item to be highlighted is an item to be displayed on the first inspection information display unit 101 or an item to be displayed on the second inspection information display unit 102. If the display item is the item to be displayed on the first inspection information display unit 101 (YES in step 903), the process proceeds to step 904. If the display item is the item to be displayed on the second inspection information display unit 102 (NO in step 903), the process proceeds to step 905.

(iv) Step 904

The control unit 214 highlights the inspection information to be displayed on the first inspection information display unit 101 of the inspection information display GUI 100.

(v) Step 905

The control unit 214 highlights the inspection information to be displayed on the second inspection information display unit 102 of the inspection information display GUI 100.

(vi) Step 906

The control unit 214 confirms the content set by the user according to the display speed setting screen 170, and determines whether a display item to be displayed is an item to be displayed on the first inspection information display unit 101 or an item to be displayed on the second inspection information display unit 102. If the display item is the item to be displayed on the first inspection information display unit 101 (YES in step 906), the process proceeds to step 907. If the display item is the item to be displayed on the second inspection information display unit 102 (NO in step 906), the process proceeds to step 908.

(vii) Step 907

The control unit 214 normally displays the inspection information to be displayed on the first inspection information display unit 101 of the inspection information display GUI 100.

(viii) Step 908

The control unit 214 normally displays the inspection information to be displayed on the second inspection information display unit 102 of the inspection information display GUI 100.

<Editing Processing of Display Inspection Information>

Figure 10:
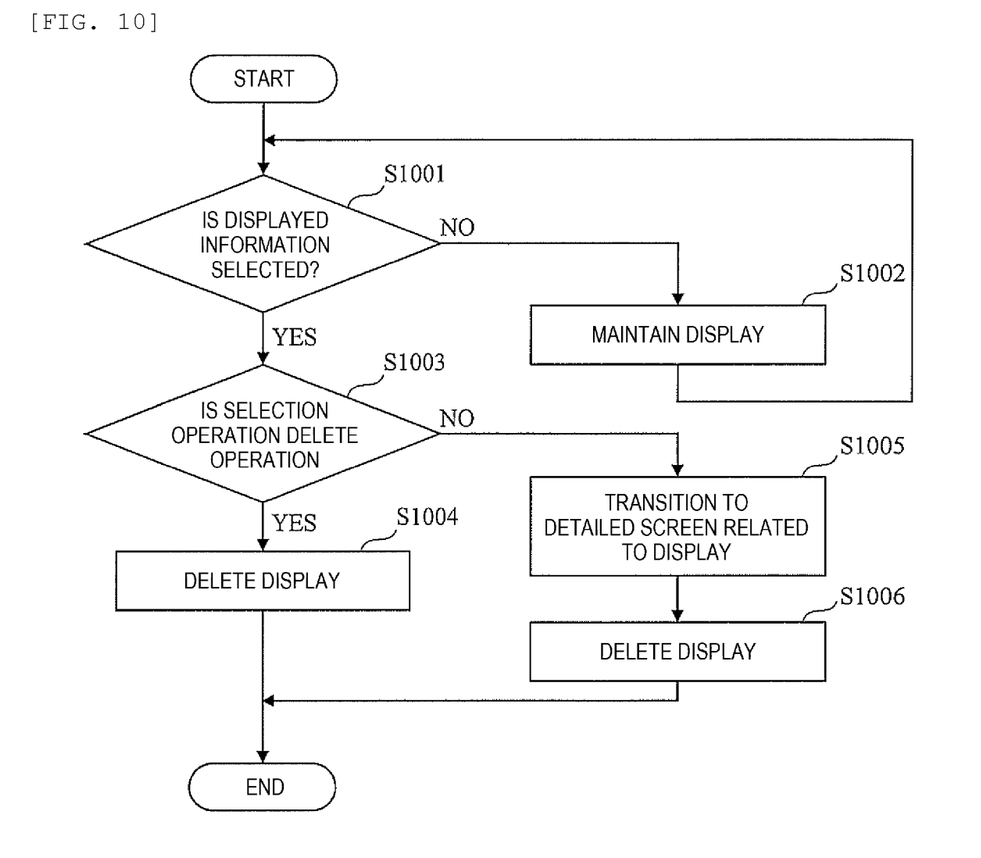
FIG. 10 is a flowchart illustrating an example of an editing processing of inspection information to be displayed, which is performed using various setting screens 120 to 170.

FIG. 10 is a flowchart illustrating an example of an editing processing (addition, deletion, and the like) of inspection information to be displayed, which is performed using various setting screens 120 to 170.

(i) Step 1001

The control unit 214 determines whether any of the inspection information displayed on the first inspection information display unit 101 or the second inspection information display unit 102 is selected by the user. If it is determined that the inspection information is selected (YES in step 1001), the process proceeds to step 1003. If it is determined that the inspection information is not selected (NO in step 1001), the process proceeds to step 1002.

(ii) Step 1002

The control unit 214 maintains a current display format and the display content of the first inspection information display unit 101 or the second inspection information display unit 102.

(iii) Step 1003

The control unit 214 determines whether an operation performed by the user is an instruction to delete the selected inspection information (direct deletion instruction) or an instruction to delete the selected inspection information after transitioning to a detailed screen (not shown: screen for showing details of inspection information) (post-confirmation deletion instruction). For example, the former can be instructed by the user double-clicking the target inspection information, and the latter can be instructed by the user one-clicking the target inspection information. If the deletion (direct deletion) of the selected inspection information is instructed (YES in step 1003), the process proceeds to step 1004. On the other hand, if the transition to the detailed screen related to the selected inspection information is instructed (NO in step 1003), the process proceeds to step 1005.

(iv) Step 1004

The control unit 214 deletes the display of the selected inspection information from the first inspection information display unit 101 or the second inspection information display unit 102.

(v) Step 1005

The control unit 214 transitions the screen from the inspection information display GUI 100 to the detailed screen related to the selected inspection information.

(vi) Step 1006

For example, in response to a deletion approval instruction from the user, the control unit 214 deletes the display of the selected inspection information from the first inspection information display unit 101 or the second inspection information display unit 102.

<Reflecting Processing of Display Setting>

Figure 11:
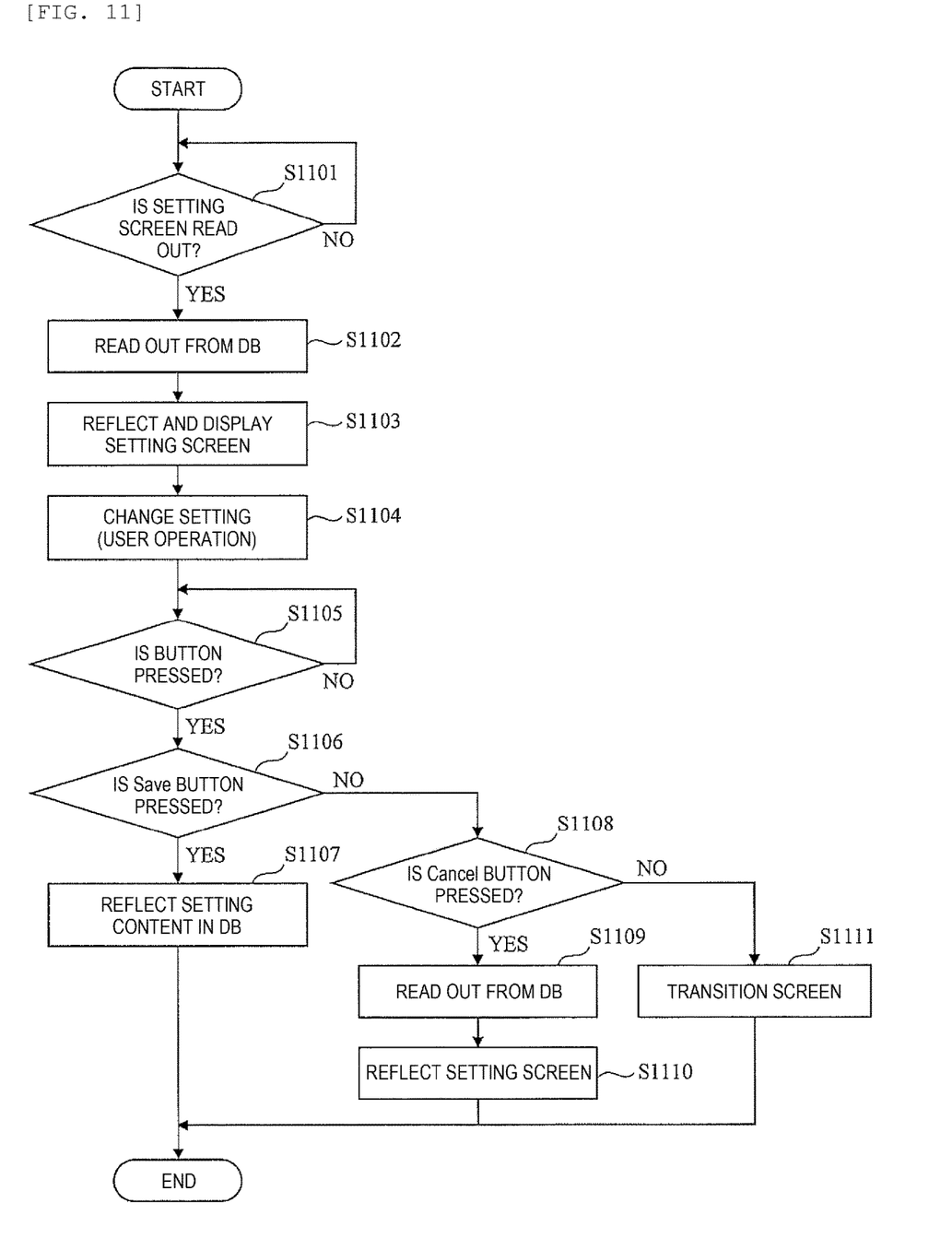
FIG. 11 is a flowchart illustrating a processing of reflecting a display setting in a database.

The PC 20 stores, for example, a database (hereinafter, referred to as a DB) related to inspection information display setting internally (for example, the storage device 216). Then, when the display setting is changed by the user, the control unit 214 updates setting information managed in the DB. FIG. 11 is a flowchart illustrating a processing of reflecting the display setting in the DB.

(i) Step 1101

The control unit 214 determines whether the display of any of the setting screens 120 to 170 shown in FIGS. 3 to 8 is instructed by the user. If the display of any of the setting screens is instructed (YES in step 1101), the process proceeds to step 1102. If the display of any of the setting screens is not instructed (NO in step 1101), the control unit 214 waits until the display of any of the setting screens is instructed.

(ii) Step 1102

The control unit 214 reads out setting related to the setting screen (designated) called by the user from the inspection information display setting stored in the DB.

(iii) Step 1103

The control unit 214 displays the designated setting screen and the settings related to the setting screen on the display screen of the display unit 217.

(iv) Step 1104

The control unit 214 accepts a setting change input by the user on the displayed setting screen, and changes the setting of each inspection information.

(v) Step 1105 and Step 1106

The control unit 214 waits until a button is pressed by the user, and when the button is pressed, the control unit 214 determines whether a Save button 129-1 displayed on a target setting screen is pressed. If it is determined that the Save button 129-1 is pressed (YES in step 1106), the process proceeds to step 1107. If it is determined that another button is pressed instead of the Save button 129-1 (NO in step 1106), the process proceeds to step 1108.

(vi) Step 1107

The control unit 214 reads out the setting displayed on the setting screen, and re-reflects all setting contents including a changed part in the DB.

(vii) Step 1108

The control unit 214 determines whether the pressed button is a Cancel button 129-2. If it is determined that the Cancel button 129-2 is pressed (YES in step 1108), the process proceeds to step 1109. If it is determined that neither the Save button 129-1 nor the Cancel button 129-2 is pressed, or if a button other than the Save button 129-1 and the Cancel button 129-2 is pressed (NO in step 1108), the process proceeds to step 1111.

(viii) Step 1109 and Step 1110

The control unit 214 does not reflect the setting on the setting screen in the DB, reads out the setting related to the called setting screen from the DB again (S1109), and returns the setting on the screen to a state (setting) at the time of the calling (S1110).

(ix) Step 1111

The control unit 214 does not reflect the setting input by the user in the DB regardless of whether the setting screen is changed, and displays the called setting screen.

(2) Second Embodiment

An automated analyzer according to a second embodiment can automatically set a display speed and highlight display of inspection information to be displayed on the first inspection information display unit 101 or the second inspection information display unit 102. In the first embodiment, the user can designate display parts of the first inspection information display unit 101 and the second inspection information display unit 102 and set the display speed and/or the highlight display by using the display speed setting screen 170 of FIG. 8.

However, setting contents are diverse and may be complicated. Therefore, in the second embodiment, the control unit 214 is configured to automatically perform the setting of the display speed and the highlight display of the inspection information to be displayed on the first inspection information display unit 101 or the second inspection information display unit 102 in consideration of an operation status of a device, a measurement request status, and display necessity setting of the inspection information set by the user. The display speed of inspection information, a setting method and means other than the highlight display are as described above. Since a setting method of sample information and a device configuration are the same as those of the first embodiment, the description thereof will be omitted.

<Automated Setting Processing of Display Speed and Automated Setting Processing of Highlight Display>

Figure 12:
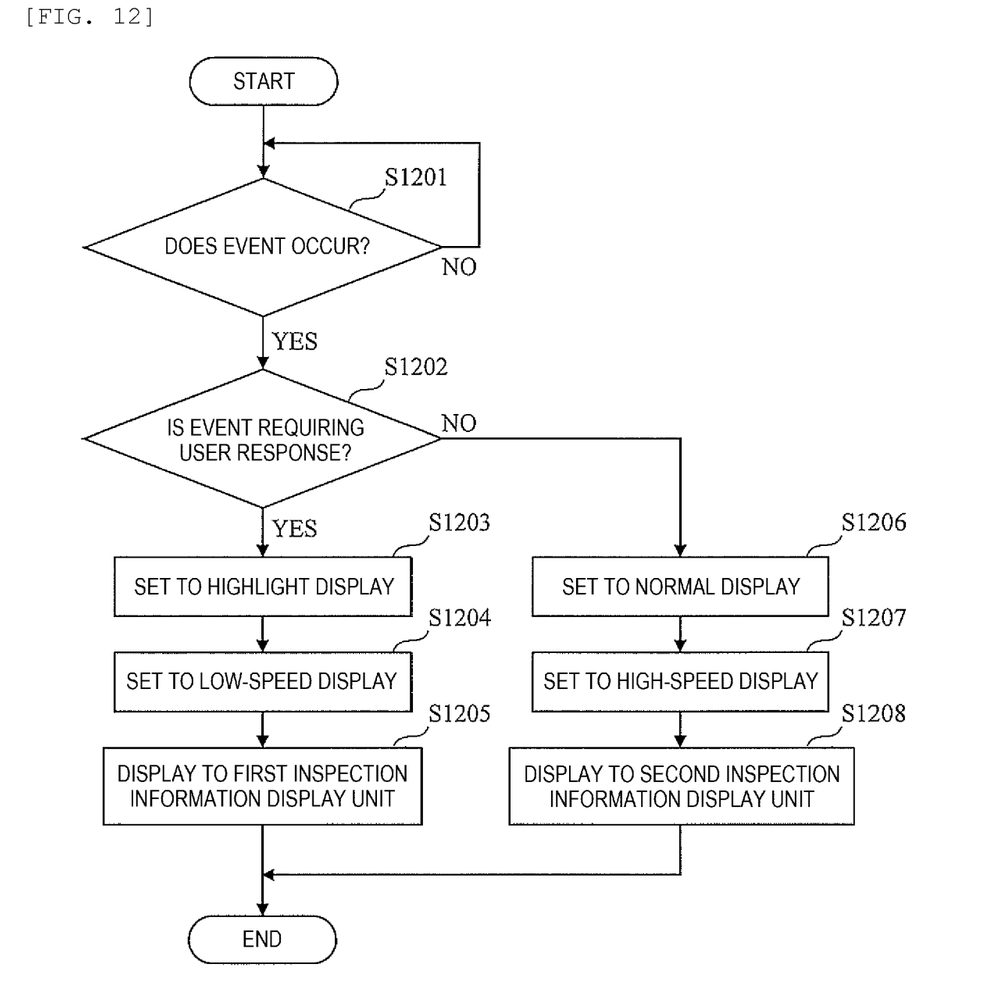
FIG. 12 is a flowchart illustrating an inspection information display condition determination processing.

FIG. 12 is a flowchart illustrating an inspection information display condition determination processing (the automated setting processing of the display speed and the automated setting processing of the highlight display). By executing the inspection information display condition determination processing according to the second embodiment, a technical effect described in the first embodiment can be expected without complicated setting of the inspection information display setting.

(i) Step 1201

The control unit 214 monitors whether an event related to the inspection information displayed and set by the user (for example, a remaining amount of a consumable is below a threshold value) occurs (waits until a target event occurs) in accordance with the inspection information display setting stored in the DB related to the inspection information display setting. If the event related to the inspection information displayed and set by the user occurs (YES in step 1201), the process proceeds to step 1202.

When the inspection information to be displayed by the user is not set, the control unit 214 monitors whether the event related to the inspection information occurs based on an initial setting content stored in the DB in advance.

(ii) Step 1202

The control unit 214 determines whether the occurred event detected in step 1201 is an event requiring immediate response of the user. The determination of the necessity of the immediate response is made based on, for example, whether an output of a result is delayed if there is no response of the user. For example, if the remaining amount of a reaction vessel, which is the consumable, is below the threshold value, it is necessary for the user to take response. If the consumable is not replenished by the user, the measurement of the current remaining amount or more cannot be continued, the device stops once, and an output of a result of a sample for which the measurement has been already requested is delayed. Further, even if abnormal suction occurs in a specific sample, it is necessary for the user to take response. When the abnormal suction occurs due to fibrin, the user must remove the fibrin from the sample and request the measurement again, which causes a further result communication delay depending on the response of the user. To prevent the result communication delay, such an operation must be responded by the user immediately after the event occurs. On the other hand, as an example in which the user does not necessarily need to take the immediate response, a result output of a designated measurement item, occurrence of re-inspection, and a report of a result output time can be mentioned.

If it is determined that the occurred event is an event that requires the response of the user (YES in step 1202), the process proceeds to step 1203. If it is determined that the occurred event is an event that does not require the response of the user (NO in step 1202), the process proceeds to step 1206.

(iii) Step 1203 and Step 1204

The control unit 214 changes the setting for the inspection information display related to the event to a highlight display and a low-speed display.

(iv) Step 1205

The control unit 214 highlights the inspection information display related to the event (inspection information item) on the first inspection information display unit 101 at a low speed. A reason why the item is displayed at the lower speed than the display determined that the immediate response is not necessary is to improve a visibility of the user.

(v) Step 1206 and Step 1207

The control unit 214 sets the inspection information display related to the event to a normal display (not highlighted) and a high-speed display.

(vi) Step 1208

The control unit 214 normally displays the inspection information display (inspection information item) related to the event on the second inspection information display unit 102 at a high speed. This is because the immediate response is not necessary, and thus it is not necessary to improve the visibility more than when necessary.

(3) Modification (i) In a sample test, it is required to shorten a turn around time (TAT: a time required from a sample introduction to a result communication). When an event leading to TAT delay occurs, it is possible to prevent TAT delay by immediately notifying the user of the response to the event in a format easily recognizable by a user.

(ii) In the present embodiment, a configuration for displaying the first inspection information display unit 101 and the second inspection information display unit 102 on an upper portion of a display screen of the display unit 217 of the automated analyzer 1 has been described. However, without being limited to this embodiment, the first inspection information display unit 101 and the second inspection information display unit 102 may be displayed on a display unit of another external PC (not shown) connected to the automated analyzer 1, for example, a PC or middleware used by the user or a clinical laboratory test information management device called a laboratory information system (LIS). In this way, the user can obtain information on a state and a result of the automated analyzer 1 without waiting near the automated analyzer 1, and can quickly respond to a situation where the user needs to operate the automated analyzer 1.

(4) Overview

In the automated analyzer 1 according to the present embodiment, the control unit 214 is configured to generate the inspection information display GUI (inspection information display GUI 100) including the first inspection information display area (for example, the first inspection information display unit 101) for displaying the plurality of pieces of inspection information, the second inspection information display area (for example, the second inspection information display unit 102) for displaying the plurality of pieces of inspection information, which are different from the inspection information displayed in the first inspection information display area, and the detailed display area (for example, the detailed information display area 111) for displaying the detailed content of inspection information, and control the display unit 217 such that when the inspection information display GUI is displayed on the screen of the display unit 217, the inspection information displayed in the first inspection information display area and the inspection information displayed in the second display area are scrolled and displayed at different speeds. The information that an operator (user) wants to know can be displayed (notified) timely and simply, and the risks of device stopping and result communication delay can be reduced.

In addition, for example, the storage unit (storage device 216) stores information on the predetermined condition that requires the user to respond to the inspection information. Then, the control unit highlights the inspection information corresponding to the predetermined condition when it is determined that it is necessary for the user to take response, among the plurality of pieces of inspection information displayed on the first and second inspection information display units 101 and 102. Specifically, when performing the highlight display, the control unit makes the scroll display speed of the inspection information corresponding to the predetermined condition slower than that in the normal display other than the highlight display. Therefore, it is possible to automatically notify the operator of the necessity of the user response appropriately (so that the operator can easily notice the necessity of the user response), and the operator can quickly respond.

The control unit 214 generates the inspection information display GUI so as to display details of the inspection information selected from the first inspection information display unit 101 and the second inspection information display unit 102 in the detail display area. In addition, the control unit 214 deletes the corresponding inspection information from the first inspection information display unit 101 and second inspection information display unit 102 in response to the input deletion instruction. Therefore, since the contents of the GUI are determined centering on the inspection information listed in the first inspection information display unit 101 and second inspection information display unit 102 (the operator can determine what kind of inspection information is displayed in each area), it is possible to notify the occurrence of an event for the inspection information that is considered to be important by the operator.

The operation buttons for individually stopping, playing, and rewinding the scroll display of the first inspection information display unit 101 and the second inspection information display unit 102 are provided in the inspection information display GUI, and the control unit 214 detects the operation on the operation button to control the scroll display of the first inspection information display unit 101 and second inspection information display unit 102. Therefore, even if the operator misses the notification of the occurrence of the event regarding certain inspection information, the operator can immediately confirm the event.

The control unit 214 generates the inspection information setting GUI for adding, deleting, or changing the inspection information displayed on the inspection information display GUI 100 and displays the inspection information setting GUI on the display unit, and adds, deletes, or changes the inspection information displayed on the inspection information display GUI 100 in response to the input of the user to the inspection information setting GUI 100. Therefore, the inspection information displayed on the inspection information display GUI 100 can be easily changed.

The control unit 214 generates, as the inspection information setting GUI 100, any one of a first setting GUI (for example, the calibration information setting screen 120) for setting whether to display the operation state of the device as the inspection information, a second setting GUI (for example, the consumable information setting screen 140) for setting whether to display the consumable information as the inspection information, a third setting GUI (for example, the measurement information setting screen 150) for setting whether to display various measurement results as the inspection information, and a fourth setting GUI (for example, the alarm information setting screen 160) for setting whether to display the warnings of various device errors as the inspection information. Therefore, it is possible to optimize the inspection information display GUI 100 for the operator.

In the above embodiments, the example in which the first inspection information display unit 101 and the second inspection information display unit 102 are controlled to be displayed in different display formats, that is, the example in which the display speed is made different, and the example in which the highlight display or the normal display is made different have been described. However, for example, various formats are conceivable, such as different fonts and different colors.

REFERENCE SIGN LIST 1 automated analyzer
100 inspection information display GUI
101 first inspection information display unit
102 second inspection information display unit
120 calibration information setting screen
130 assay reagent information setting screen
140 consumable information setting screen
150 measurement information setting screen
160 alarm information setting screen
170 display speed setting screen 201 rack
202 rack transport line
204 reagent cold insulation unit
205 incubator (reaction disk)
206 sample dispensing mechanism
207 reagent dispensing mechanism
210 sample vessel
211 reagent vessel
212 reagent disc cover
213 reaction vessel
214 control unit
215 operation unit
216 storage device
217 display unit (display device)

The invention claimed is:

1. An automatic analyzer comprising:
a sample storage configured to store a plurality of samples to be analyzed;
a reagent storage configured to store a plurality of reagents;
a reaction vessel configured to receive a sample and a reagent;
an analysis operation unit configured to analyze a reaction liquid obtained by dispensing the reagent and the sample into the reaction vessel;
a control unit configured to control an operation of the analysis operation unit;
a storage unit configured to store analysis results from the analysis operation unit and information on a consumable used by the analysis operation unit; and
a display unit configured to display the analysis results and inspection information, wherein
the control unit generates an inspection information setting GUI for adding, deleting, or changing the inspection information displayed on an inspection information display GUI and displays the inspection information setting GUI on the display unit, and adds, deletes or changes the inspection information displayed on the inspection information display GUI in response to an input of a user to the inspection information setting GUI, and
the control unit is configured to:
generate the inspection information display GUI including a first inspection information display area for displaying first inspection information which is important information needed to be handled by the user from among the inspection information and a second inspection information display area for displaying second inspection information, which is different from the first inspection information, and which is not important information needed to be handled by a user from among the inspection information, and
control the display unit such that when the inspection information display GUI is displayed on a screen of the display unit, the first inspection information is scrolled at a first speed and the second inspection information is scrolled at a second speed which is higher than the first speed, wherein
the scrolling of the first inspection information and the second inspection information can be individually stopped and played by operation by the user on the display unit to allow the user to confirm a particular first or second inspection information, the inspection information includes device status information, consumable information, measurement information, and alarm information, the control unit generates the inspection information display GUI such that any one or a combination of the inspection information is displayed in the first inspection information display area and any one or a combination of the inspection information other than the inspection information displayed in the first inspection information display area is displayed in the second inspection information display area, and the control unit monitors whether an event occurs based on a remaining amount of a consumable based on the consumable information of a particular inspection item being below a threshold value, and when the event occurs, the control unit determines whether the event requires an immediate response of the user, and when the control unit determines that the event requires the immediate response of the user, the control unit changes a setting for the particular inspection item on the information display to highlight display, scrolls the particular inspection item at the first speed and displays the particular inspection item in the first inspection information display area.

2. The automatic analyzer according to claim 1, wherein the control unit deletes the corresponding inspection information from the first and/or second inspection information display area in response to an input deletion instruction.

3. The automatic analyzer according to claim 1, wherein an operation unit for individually stopping, reproducing, and rewinding the scroll display of the first and second inspection information display areas is provided in the inspection information display GUI, and the control unit detects an operation on the operation unit to control the scroll display of the first and second inspection information display areas.

4. The automatic analyzer according to claim 3, wherein the operation unit is an operation button or a touch panel.

5. The automatic analyzer according to claim 1, wherein the control unit generates, as the inspection information setting GUI, any one of a first setting GUI for setting whether to display an operation state of a device as the inspection information, a second setting GUI for setting whether to display consumable information as the inspection information, a third setting GUI for setting whether to display various measurement results as the inspection information, and a fourth setting GUI for setting whether to display warnings of various device errors as the inspection information.

* * * * *